(12) United States Patent
Kawamura et al.

(10) Patent No.: US 11,746,054 B2
(45) Date of Patent: Sep. 5, 2023

(54) ZIRCONIA SINTERED BODY AND METHOD FOR MANUFACTURING THE SAME

(71) Applicant: TOSOH CORPORATION, Yamaguchi (JP)

(72) Inventors: Kiyotaka Kawamura, Yamaguchi (JP); Akiko Ito, Yamaguchi (JP); Hiroyuki Fujisaki, Yamaguchi (JP); Sho Azechi, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 17 days.

(21) Appl. No.: 17/241,274

(22) Filed: Apr. 27, 2021

(65) Prior Publication Data

US 2021/0246075 A1    Aug. 12, 2021

Related U.S. Application Data

(62) Division of application No. 16/313,393, filed as application No. PCT/JP2018/010748 on Mar. 19, 2018, now Pat. No. 11,021,401.

(51) Int. Cl.
| | |
|---|---|
| *C04B 35/488* | (2006.01) |
| *A61C 13/083* | (2006.01) |
| *C04B 35/64* | (2006.01) |

(52) U.S. Cl.
CPC ........ *C04B 35/4885* (2013.01); *A61C 13/083* (2013.01); *C04B 35/64* (2013.01); *A61C 2201/002* (2013.01); *C04B 2235/3217* (2013.01); *C04B 2235/3246* (2013.01); *C04B 2235/656* (2013.01); *C04B 2235/785* (2013.01); *C04B 2235/786* (2013.01)

(58) Field of Classification Search
CPC . C04B 35/486; C04B 35/488; C04B 35/4885; A61C 13/083
See application file for complete search history.

(56) References Cited

U.S. PATENT DOCUMENTS

| | | | | |
|---|---|---|---|---|
| 6,168,745 | B1 ‡ | 1/2001 | Jue ........................ | C04B 35/486 264/234 |
| 9,737,383 | B2 ‡ | 8/2017 | Fujisaki ................. | C04B 35/64 |
| 10,532,008 | B2 * | 1/2020 | Balasubramanian ....................... | C04B 35/486 |
| 2010/0003630 | A1 ‡ | 1/2010 | Yamashita ............ | C04B 35/486 433/8 |
| 2011/0027742 | A1 ‡ | 2/2011 | Fujisaki ................. | A61K 6/824 433/8 |
| 2014/0370453 | A1 ‡ | 12/2014 | Fujisaki ............. | A61C 13/0022 433/8 |
| 2016/0016853 | A1 * | 1/2016 | Yamada .................. | C04B 35/64 501/134 |
| 2016/0310245 | A1 ‡ | 10/2016 | Fujisaki ............. | A61C 13/0022 |
| 2018/0235847 | A1 * | 8/2018 | Balasubramanian .. | A61K 6/818 |
| 2020/0107996 | A1 * | 4/2020 | Balasubramanian .. | A61K 6/818 |

FOREIGN PATENT DOCUMENTS

| | | |
|---|---|---|
| EP | 0 637 576 | 2/1995 |
| GB | 2280670 A | 2/1995 |
| JP | 60081060 A * | 5/1985 |
| JP | 7-82018 | 3/1995 |
| JP | 7-165465 | 6/1995 |
| JP | 09-208306 | 8/1997 |
| JP | 2004-137128 | 5/2004 |
| JP | 2008-50247 | 3/2008 |
| JP | 2010-150063 | 7/2010 |
| JP | 2011-73907 | 4/2011 |
| JP | 2015-143178 | 8/2015 |
| JP | 2016-108176 | 6/2016 |
| JP | 2018-52806 | 4/2018 |
| WO | 2015/098765 | 7/2015 |

OTHER PUBLICATIONS

Machine translation of JP60081060, May 1985 (Year: 1985).*
Wits et al "Phase evolution of yttria-stabilized zirconia thermal barrier coatings studied by rievtceld refinement of x-ray powder diffraction patterns", J, Am. Ceram, Soc., 90[9] pp. 2935-2940. (Year: 2007).‡
Extended European Search Report issued in European Patent Application No. 18803851.7 dated Sep. 30, 2021.
"Material Database", Jan. 25, 1989, p. 97.
International Search Report issued in International Patent Application No. PCT/JP2018/010748, dated Jun. 12, 2018 and English Translation thereof.
Written Opinion of the International Searching Authority issued in International Patent Application No. PCT/JP2018/010748, dated Dec. 6, 2018 and English Translation thereof.

\* cited by examiner
‡ imported from a related application

*Primary Examiner* — Karl E Group
(74) *Attorney, Agent, or Firm* — GREENBLUM & BERNSTEIN, P.L.C.

(57) ABSTRACT

A method for manufacturing a zirconia sintered body includes molding a powder composition that has a yttria content of more than 3% by mole and 5.2% by mole or less and that contains a first zirconia powder having a yttria content of 2% by mole or more and 4% by mole or less and a second zirconia powder having a yttria content of more than 4% by mole and 6% by mole or less to obtain a green body, and sintering the green body to obtain a sintered body.

12 Claims, 1 Drawing Sheet

ZIRCONIA SINTERED BODY AND METHOD FOR MANUFACTURING THE SAME

CROSS-REFERENCE TO RELATED APPLICATIONS

This is a divisional application of U.S. patent application Ser. No. 16/313,393, filed Dec. 26, 2018 which is a U.S. National Phase under 35 U.S.C. § 371 of International Patent Application No. PCT/JP2018/010748, filed Mar. 19, 2018. The disclosure of each of the above-mentioned documents, including the specification, drawings, and claims, is incorporated herein by reference in its entirety.

TECHNICAL FIELD

The present invention relates to a zirconia sintered body having both translucency and high strength and a method for manufacturing the same.

BACKGROUND ART

Zirconia sintered bodies are used not only as structural materials and decorative members but also as dental materials, since they have high mechanical strength and high aesthetic properties due to their translucency (PTL 1 to PTL 4). A zirconia sintered body used as a dental material is required to have a high translucency of a total light transmittance of 40% or more and a high bending strength of 800 MPa or more (PTL 1).

An example of the zirconia sintered body that satisfies such a requirement, a zirconia sintered body manufactured by hot isostatic pressing (hereinafter, referred to as "HIP") and having a total light transmittance of 43% or more at a sample thickness of 0.5 mm, a three-point bending strength of 1,700 MPa or more and an yttria content of 2% to 4% by mole has been disclosed (PTL 2). However, the practical use of the zirconia sintered body disclosed in PTL 2 is limited because HIP requires a large apparatus.

On the other hand, studies have been conducted on a zirconia sintered body having both high mechanical strength and high translucency and capable of being obtained without HIP and a method for manufacturing the zirconia sintered body.

PTL 1 discloses a method for molding and sintering a zirconia powder which has an yttria content of about 3% by mole and in which the BET specific surface area and crystallinity are controlled. PTL 1 discloses that a zirconia sintered body having a total light transmittance of 41.20% to 44.06% to D65 light at a sample thickness of 0.5 mm and a bending strength of 860 to 891 MPa is obtained by firing at a maximum temperature of 1,450° C. for 2 hours. However, the total light transmittance of this zirconia sintered body is only less than 30% at maximum when converted into a total light transmittance to D65 light at a sample thickness of 1 mm (hereinafter, also simply referred to as "total light transmittance"). The zirconia sintered body disclosed in PTL 1 does not have translucency sufficient for use as a dental material.

Regarding a zirconia sintered body having mechanical strength and translucency that are high enough to be practically used as a dental material, PTL 3 discloses that a zirconia sintered body is obtained by pressureless sintering of a zirconia powder which has an yttria content of 2% to 4% by mole and in which a sintering shrinkage rate from a relative density of 70% to a relative density of 90%, a BET specific surface area, etc. are controlled, and the zirconia sintered body has a total light transmittance of 35% or more and a three-point bending strength of 1,000 MPa or more.

PTL 4 discloses a zirconia sintered body having both high mechanical strength and high translucency and having translucency high enough to be applied to a dental material for a front tooth, and a method for manufacturing such a zirconia sintered body without HIP. The zirconia sintered body disclosed in PTL 4 is a zirconia sintered body obtained by pressureless sintering and having an yttria content of more than 4% by mole and 6.5% by mole or less and has a total light transmittance of 42% or more and a three-point bending strength of 550 to 870 MPa.

The zirconia sintered bodies disclosed in PTL 3 and PTL 4, which can be manufactured by pressureless sintering, are used as practical dental materials because they have high mechanical strength and high translucency.

CITATION LIST

Patent Literature

PTL 1: Japanese Unexamined Patent Application Publication No. 2016-108176
PTL 2: Japanese Unexamined Patent Application Publication No. 2008-050247
PTL 3: Japanese Unexamined Patent Application Publication No. 2010-150063
PTL 4: Japanese Unexamined Patent Application Publication No. 2015-143178

SUMMARY OF INVENTION

Technical Problem

The zirconia sintered bodies disclosed in PTL 3 and PTL 4 satisfy mechanical strength and translucency that are required for dental materials. However, in an actual use, different dental materials are appropriately used depending on the application position, for example, among dental materials, a material having higher strength is used as a dental material for a back tooth, and a dental material having higher translucency is used as a dental material for a front tooth. PTL 4 discloses only a single zirconia sintered body having both high mechanical strength and high translucency, specifically, having a three-point bending strength of 870 MPa and a total light transmittance of 44%. However, in order to repeatedly manufacture this zirconia sintered body, it is necessary to control manufacturing conditions in painstaking detail.

In view of these problems, an object of the present invention is to provide a zirconia sintered body capable of being widely used as a dental material, in particular, a zirconia sintered body capable of being applied to both a dental material for a back tooth and a dental material for a front tooth and a simple and easy method for manufacturing the zirconia sintered body.

Solution to Problem

The inventors of the present invention conducted studies on a zirconia sintered body having both mechanical properties and translucency that satisfy properties required for a dental material, in particular, both a dental material for a front tooth and a dental material for a back tooth and a method for manufacturing the zirconia sintered body. As a result, it was found that such a zirconia sintered body can be simply and easily manufactured by controlling a state of a raw material powder, and this finding led to the completion of the present invention.

Specifically, the gist of the present invention is as follows.

[1] A zirconia sintered body having an yttria content of more than 3% by mole and 5.2% by mole or less and an yttrium concentration distribution in which a maximum of a frequency is 7.5% or less, the yttrium concentration distribution being obtained by a quantitative analysis of elements of an energy dispersive X-ray spectrum.

[2] The zirconia sintered body according to [1], in which a crystal phase of the zirconia sintered body comprises a tetragonal phase including a T phase and a T* phase.

[3] The zirconia sintered body according to [1] or [2], in which the zirconia sintered body has an average crystal grain size of more than 0.41 μm and 1.5 μm or less.

[4] A method for manufacturing a zirconia sintered body, the method comprising a molding step of molding a powder composition that has an yttria content of more than 3% by mole and 5.2% by mole or less and that contains a first zirconia powder having an yttria content of 2% by mole or more and 4% by mole or less and a second zirconia powder having an yttria content of more than 4% by mole and 6% by mole or less to obtain a green body; and a sintering step of sintering the green body to obtain a sintered body.

[5] The manufacturing method according to [4], in which the powder composition contains alumina.

[6] The manufacturing method according to [4] or [5], in which the powder composition has a BET specific surface area of 5 $m^2/g$ or more and less than 17 $m^2/g$.

[7] The manufacturing method according to any one of [4] to [6], in which a weight ratio of the first zirconia powder to the second zirconia powder is 35% by weight:65% by weight to 65% by weight:35% by weight.

[8] The manufacturing method according to any one of [4] to [7], in which the first zirconia powder has an yttria content of 2% by mole or more and 3.5% by mole or less, and the second zirconia powder has an yttria content of 4.5% by mole or more and 5.7% by mole or less.

[9] The manufacturing method according to any one of [4] to [8], in which a sintering temperature in the sintering step is 1,400° C. or higher and 1,600° C. or lower.

Advantageous Effects of Invention

The present invention can provide a zirconia sintered body capable of being widely used as a dental material, in particular, a zirconia sintered body capable of being applied to both a dental material for a back tooth and a dental material for a front tooth and a manufacturing method by which such a zirconia sintered body can be simply and easily manufactured.

DESCRIPTION OF EMBODIMENTS

Figure 1:
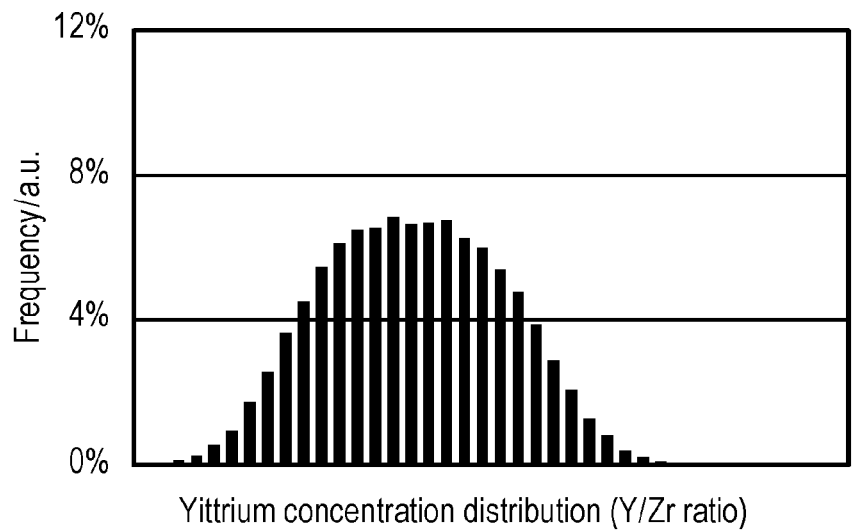
FIG. 1 A graph showing the yttrium concentration distribution of Example 3.

Hereinafter, embodiments of a method for manufacturing a zirconia sintered body according to the present invention will be described.

A manufacturing method according to an embodiment of the present invention comprises a molding step of molding a powder composition that has an yttria content of more than 3% by mole and 5.2% by mole or less and that contains a first zirconia powder having an yttria content of 2% by mole or more and 4% by mole or less and a second zirconia powder having an yttria content of more than 4% by mole and 6% by mole or less (hereinafter, also simply referred to as a "powder composition") to obtain a green body.

The powder composition is used in the molding step. The powder composition has an yttria content of more than 3% by mole and 5.2% by mole or less. When the yttria content is 3% by mole or less, the resulting zirconia sintered body has a total light transmittance of 42% or less to D65 light at a sample thickness of 1 mm, and thus the range of applications to dental materials is limited. In contrast, when the yttria content exceeds 5.2% by mole, a zirconia sintered body having a three-point bending strength of 800 MPa or more, which is required for a dental material, is not obtained even by the manufacturing method according to an embodiment of the present invention.

The yttria content of the powder composition is 3.5% by mole or more and 4.8% by mole or less, preferably 3.8% by mole or more and 4.6% by mole or less, and preferably 3.8% by mole or more and 4.3% by mole or less.

The powder composition contains a first zirconia powder having an yttria content of 2% by mole or more and 4% by mole or less (hereinafter, also referred to as a "low yttria powder") and a second zirconia powder having an yttria content of more than 4% by mole and 6% by mole or less (hereinafter, also referred to as a "high yttria powder"). The zirconia sintered body obtained by sintering such a powder composition has a tendency that the mechanical strength improves with an increase in the average crystal grain size. Therefore, a zirconia sintered body having both mechanical strength and translucency that are equal to or higher than the properties required for a dental material can be obtained without controlling manufacturing conditions in detail.

The yttria content of the low yttria powder is 2% by mole or more and 4% by mole or less, preferably 2% by mole or more and 3.5% by mole or less, and more preferably 2.3% by mole or more and 3.5% by mole or less. The yttria content of the high yttria powder is more than 4% by mole and 6% by mole or less, preferably 4% by mole or more and 5.7% by mole or less, and more preferably 4.5% by mole or more and 5.7% by mole or less.

In an embodiment of the present invention, the powder composition preferably contains a zirconia powder having an yttria content of 2.3% by mole or more and 3.5% by mole or less as the low yttria powder and a zirconia powder having an yttria content of 5.2% by mole or more and 5.7% by mole or less as the high yttria powder.

The content ratio of the low yttria powder to the high yttria powder of the powder composition is not limited as long as the powder composition has a desired yttria content. The ratio may be low yttria powder:high yttria powder=1% by weight:99% by weight to 99% by weight:1% by weight in terms of weight ratio of the low yttria powder to the high yttria powder, though the content ratio of the low yttria powder to the high yttria powder of the powder composition varies depending on the yttria contents of the powders. The weight ratio is more preferably low yttria powder:high yttria powder=20% by weight:80% by weight to 80% by weight: 20% by weight, and still more preferably 35% by weight: 65% by weight to 65% by weight:35% by weight.

Each of the low yttria powder and the high yttria powder can be manufactured by a manufacturing method including a hydrolysis step of obtaining a hydrated zirconia sol by hydrolysis of an aqueous solution of a zirconium salt, a drying step of mixing an yttrium compound to the resulting hydrated zirconia sol and then drying the resulting mixture to obtain a dry powder, and a calcination step of calcining the dry powder to obtain a calcined powder. A preferred method for manufacturing a low yttria powder and a high yttria powder, for example, is a manufacturing method including mixing at least one of yttrium oxide or yttrium chloride with a hydrated zirconia sol obtained by hydrolyzing at least one selected from the group consisting of zirconium oxychloride, zirconyl nitrate, zirconium chloride and zirconium sulfate, subsequently drying the resulting mixture in air at 80° C. or higher and 200° C. or lower, and subsequently calcining the dry mixture in air at 1,050° C. or higher and 1,250° C. or lower.

The powder composition may contain alumina ($Al_2O_3$). The alumina content of the powder composition is 0% by weight or more and 0.1% by weight or less, preferably 0% by weight or more and less than 0.1% by weight, and more preferably 0% by weight or more and 0.075% by weight or less in terms of the ratio of the weight of alumina to the weight of the powder composition. In the case where the powder composition contains alumina, the alumina content is more than 0% by weight and 0.1% by weight or less, preferably more than 0% by weight and less than 0.1% by weight, more preferably more than 0% by weight and 0.075% by weight or less, and still more preferably 0.01% by weight or more and 0.075% by weight or less in terms of the ratio of the weight of alumina to the weight of the powder composition.

The crystallite size of the powder composition is 200 Å or more and 400 Å or less, and preferably 300 Å or more and 400 Å or less. The crystallite size of the powder composition can be obtained from an XRD peak (hereinafter, also referred to as a "main XRD peak") of the tetragonal (111) plane and the cubic (111) plane in powder X-ray diffraction (hereinafter, referred to as "XRD") measurement by using the formula below.

$$\text{Crystallite size} = \kappa \lambda / \beta \cos \theta$$

In the above formula, $\kappa$ represents a Scherrer constant ($\kappa=1$), $\lambda$ represents the wavelength of the measured X-ray ($\lambda=1.541862$ Å when CuKα rays are used as a radiation source), $\beta$ represents a full width (°) at half maximum of the main XRD peak, and $\theta$ represents the Bragg angle of the main XRD peak.

Note, that the main XRD peak is an XRD peak having a peak top at $2\theta=30.1°$ to $30.2°$ in XRD in which CuKα rays are used as a radiation source. The peak is an XRD peak in which the tetragonal (111) plane and the cubic (111) plane overlap each other. To calculate the crystallite size, the main XRD peak is subjected to waveform processing without separating the tetragonal and cubic phase peaks. The Bragg angle ($\theta$) of the main XRD peak after the waveform processing and the full width ($\beta$) at half maximum of the main XRD peak after mechanical spreading width correction are determined.

In the powder composition, a ratio of the tetragonal phase and the cubic phase (hereinafter, also referred to as "T+C phase ratio") obtained by the formula below is preferably 60% or more, and more preferably 65% or more.

$$T+C \text{ phase ratio } (\%) = 100 - fm(\%)$$

In the above formula, fm represents a monoclinic phase ratio obtained from an XRD pattern.

Preferably, the powder composition, the low yttria powder and the high yttria powder have substantially the comparable BET specific surface area and average particle size from the viewpoint that the physical properties of the powder composition are made homogeneous.

A preferred BET specific surface area may be 5 $m^2/g$ or more and less than 17 $m^2/g$. The BET specific surface area is preferably 5 $m^2/g$ or more and 15 $m^2/g$ or less. A preferred average particle size may be 0.30 μm or more and 0.60 μm or less. The average particle size is preferably 0.35 μm or more and 0.55 μm or less, and more preferably 0.40 μm or more and 0.50 μm or less.

The powder composition may be manufactured by any method as long as the powder composition contains a low yttria powder and a high yttria powder and the powder composition having a desired composition is obtained. The powder composition is simply and easily obtained by mixing a low yttria powder and a high yttria powder. Any mixing method may be employed as long as the two yttria powders are uniformly mixed. At least one of dry mixing or wet mixing, and furthermore, wet mixing can be employed. A preferred mixing method is mixing in a water solvent. For the purpose of uniform mixing, non-granulated powders, such as calcined powders, are preferably used as the low yttria powder and the high yttria powder.

In the case the powder composition contains alumina, the powder composition may be obtained by mixing the low yttria powder and the high yttria powder, and subsequently mixing the resulting mixed powder with alumina. However, the powder composition is preferably obtained by mixing alumina with at least one of the low yttria powder or the high yttria powder, and subsequently mixing the low yttria powder and the high yttria powder.

The powder composition used in the molding step is preferably a granulated powder. A granulated powder composition has high fluidity and therefore is easily densified during sintering. Examples of properties of a granulated powder include an average granule size of 30 μm or more and 80 μm or less and a bulk density of 1.10 $g/cm^3$ or more and 1.40 $g/cm^3$ or less.

The granulated powder is obtained by mixing a powder composition and an organic binder, and subjecting the resulting mixture to spray-drying. The content of the organic binder of the powder composition may be 1% by weight or more and 5% by weight or less relative to the weight of the powder composition.

In the molding step, any molding method may be employed as long as a green body having a desired shape is obtained. The molding method is, for example, at least one selected from the group consisting of press molding, cold isostatic pressing, sheet molding and injection molding.

The green body may have any shape. The shape may be at least one selected from the group consisting of a spherical shape, a substantially spherical shape, an elliptical shape, a disk shape, a columnar shape, a cubic shape, a rectangular parallelepiped shape, a polyhedral shape and a substantially polyhedral shape.

The manufacturing method according to an embodiment of the present invention may include a pre-sintering step of pre-sintering the green body obtained in the molding step to obtain a pre-sintered body. The pre-sintering step is a step between the molding step and a sintering step. The pre-sintering step provides a zirconia pre-sintered body having an yttria content of more than 3% by mole and 5.2% by mole or less, preferably 3.5% by mole or more and 4.8% by mole or less, more preferably 3.8% by mole or more and 4.6% by mole or less, and still more preferably 3.8% by mole or more and 4.3% by mole or less. The pre-sintered body is a green body at an initial stage of sintering and has a structure including necking between particles. In the pre-sintering step, the pre-sintered body may be processed so as to have any shape.

The pre-sintering can be conducted by heat treatment at a pre-sintering temperature of 600° C. or higher and 1,400° C. or lower, preferably 600° C. or higher and lower than 1,400° C., more preferably 600° C. or higher and 1,200° C. or lower, and still more preferably 800° C. or higher and 1,100° C. or lower.

The holding time at the pre-sintering temperature is, for example, 1 hour or more and 5 hours or less, preferably 1 hour or more and 3 hours or less, and more preferably 1 hour or more and 2 hours or less.

The pre-sintering atmosphere should be an atmosphere other than a reducing atmosphere and is preferably at least any of an oxygen atmosphere or an air atmosphere. An air atmosphere is simply and easily used.

In the sintering step, the green body obtained in the molding step is sintered to obtain a sintered body. This step provides a zirconia sintered body having an yttria content of more than 3% by mole and 5.2% by mole or less, preferably 3.5% by mole or more and 4.8% by mole or less, more preferably 3.8% by mole or more and 4.6% by mole or less, and still more preferably 3.8% by mole or more and 4.3% by mole or less.

When the manufacturing method of the present invention includes the pre-sintering step, the pre-sintered body may be sintered instead of the green body in the sintering step.

The sintering temperature in the sintering step is 1,400° C. or higher and 1,600° C. or lower, preferably 1,420° C. or higher and 1,580° C. or lower, more preferably 1,440° C. or higher and 1,560° C. or lower, and particularly preferably 1,480° C. or higher and 1,560° C. or lower. The sintering temperature in another embodiment is 1,450° C. or higher and 1,650° C. or lower, preferably 1,500° C. or higher and 1,650° C. or lower, more preferably 1,500° C. or higher and 1,650° C. or lower, and still more preferably 1,550° C. or higher and 1,650° C. or lower.

The temperature-increasing rate in the sintering step may be 150° C./h or more and 800° C./h or less and is preferably 150° C./h or more and 700° C./h or less, and more preferably 200° C./h or more and 600° C./h or less. Under such a condition, the green body can be sintered at the sintering temperature while suppressing progress of sintering in the temperature-increasing process.

The holding time at the sintering temperature (hereinafter, also simply referred to as a "holding time") varies depending on the sintering temperature. The holding time is, for example, 1 hour or more and 5 hours or less, preferably 1 hour or more and 3 hours or less, and more preferably 1 hour or more and 2 hours or less.

The sintering atmosphere should be an atmosphere other than a reducing atmosphere and is preferably at least any of an oxygen atmosphere or an air atmosphere. An air atmosphere is simply and easily used.

A particularly preferred sintering step may include sintering at atmospheric pressure, at a temperature-increasing rate of 700° C./h or less and at a sintering temperature of 1,440° C. or higher and 1,560° C. or lower.

In the sintering step, any sintering method may be employed. The sintering method may be at least one selected from the group consisting of pressureless sintering, HIP, PSP, and vacuum sintering. A typical means for enhancing translucency is to use, after a sintered body is obtained by pressureless sintering, a special sintering method such as HIP or another pressure sintering method or SPS. However, such special sintering methods not only complicate the manufacturing process, but also cause an increase in the manufacturing cost. Accordingly, the sintering step in an embodiment of the present invention preferably includes pressureless sintering, and more preferably includes only pressureless sintering. The term "pressureless sintering" refers to a method of sintering a green body by simply heating the green body without applying any external force during sintering. An specific example of pressureless sintering is sintering under atmospheric pressure.

One feature in the manufacturing method according to an embodiment of the present invention is that, with an increase in the sintering temperature, a decrease in mechanical strength due to an increase in the average crystal grain size of the resulting zirconia sintered body tends to be significantly suppressed, and furthermore, with an increase in the average crystal grain size, mechanical strength increases in some cases. Accordingly, a zirconia sintered body having a higher total light transmittance while maintaining high mechanical strength is easily obtained. Therefore, a zirconia sintered body having both mechanical properties and translucency that satisfy properties required for both a dental material for a front tooth and a dental material for a back tooth can be simply and easily manufactured without controlling manufacturing conditions in detail.

According to another aspect of the present invention, an embodiment of the present invention may be a method for manufacturing a zirconia pre-sintered body, the method including a molding step of molding a powder composition that contains a first zirconia powder having an yttria content of 2% by mole or more and 4% by mole or less and a second zirconia powder having an yttria content of more than 4% by mole and 6% by mole or less and that has an yttria content of more than 3% by mole and 5.2% by mole or less to obtain a green body; and pre-sintering the green body to obtain a pre-sintered body.

The zirconia sintered body according to an embodiment of the present invention is a sintered body having a wider yttria concentration distribution than existing sintered bodies. Specifically, the sintered body according to an embodiment of the present invention is a zirconia sintered body having an yttria content of more than 3% by mole and 5.2% by mole or less and an yttrium concentration distribution in which a maximum of a frequency is 7.5% or less, the yttrium concentration distribution being obtained by a quantitative analysis of elements of an energy dispersive X-ray spectrum.

The sintered body according to an embodiment of the present invention has an yttria content of 3.5% by mole or more and 4.8% by mole or less, preferably 3.8% by mole or more and 4.6% by mole or less, and more preferably 3.8% by mole or more and 4.3% by mole or less.

In an embodiment of the present invention, the yttria content of the zirconia sintered body is an average composition of the sintered body obtained by the composition analysis and can be measured by ICP analysis.

In the sintered body according to an embodiment of the present invention, the maximum of a frequency of an yttrium concentration distribution in a quantitative analysis of elements of an energy dispersive X-ray spectrum (hereinafter, also simply referred to as a "frequency") is 7.5% or less and preferably 7.0% or less.

A maximum of the frequency (hereinafter, also referred to as a "maximum frequency") of 7.5% or less means that the sintered body according to an embodiment of the present invention has a large number of regions having different yttria concentrations therein. The yttria content in the above range and this yttrium concentration distribution of the sintered body are believed to be one reason for contribution to an improvement in mechanical properties of the sintered body. The maximum frequency may be 3.0% or more, and further 5.0% or more.

The quantitative analysis of elements of an EDS spectrum is performed by obtaining an EDS spectrum of a scanning electron microscope (hereinafter, also referred to as a "SEM") observation image of a sintered body, and quantifying the intensities of characteristic X-rays of zirconium (Zr) and yttrium (Y) of the EDS spectrum. The quantification of the EDS spectrum may include measurement at 40,000 positions or more that are selected at random on the SEM observation image. The yttrium concentration is preferably obtained as a ratio of the intensity of yttrium to the intensity of zirconium (hereinafter, also referred to as a "Y/Zr ratio"). The yttrium concentration distribution is preferably an yttrium concentration distribution divided into regions each corresponding to a certain yttrium concentration range and may be an yttrium concentration distribution divided into concentration ranges at intervals of 0.5% in terms of the Y/Zr ratio. The frequency is a ratio (%) of the number of measurement points corresponding to each yttrium concentration relative to the total number of measurement points in the quantification of the EDS spectrum. The sintered body according to an embodiment of the present invention has a homogeneous composition on the surface and inside thereof. Therefore, the yttrium concentration distribution of the whole sintered body can be measured by EDS observation of the surface.

The crystal phase of the sintered body according to an embodiment of the present invention comprises a tetragonal phase. The tetragonal phase preferably includes the T phase and the T* phase. A ratio of the T* phase to the T phase in the crystal phase (hereinafter, also referred to as "T*/T ratio") is 62% or more and less than 100%, and preferably 65% or more and less than 100%. More preferably, the T*/T ratio is 76% or more and less than 100%, and further 76% or more and 90% or less because the mechanical strength increases.

The sintered body of an embodiment of the present invention may contain alumina ($Al_2O_3$). The alumina content of the sintered body of an embodiment of the present invention may be 0% by weight or more and 0.1% by weight or less, and is preferably 0% by weight or more and less than 0.1% by weight, and more preferably 0% by weight or more and 0.075% by weight or less, in terms of a ratio of the weight of alumina to the weight of the sintered body according to an embodiment of the present invention. When the sintered body according to an embodiment of the present invention contains alumina, the alumina content may be more than 0% by weight and 0.1% by weight or less, and is preferably more than 0% by weight and less than 0.1% by weight, more preferably more than 0% by weight and 0.075% by weight or less, and still more preferably 0.01% by weight or more and 0.075% by weight or less, in terms of a ratio of the weight of alumina to the weight of the sintered body according to an embodiment of the present invention.

Mechanical strength and translucency of a zirconia sintered body are affected by the average crystal grain size, and these properties have a trade-off relationship. Specifically, when the average crystal grain size is decreased, mechanical strength increases but translucency decreases. On the other hand, when the average crystal grain size is increased, mechanical strength decreases but translucency increases. In order to realize both mechanical strength and translucency that are required for a dental material, hitherto, high translucency is achieved by controlling the yttria content to more than 3% by mole, and high mechanical strength is achieved by controlling the average crystal grain size to about 0.41 µm.

In contrast, even when the sintered body according to an embodiment of the present invention has an average crystal grain size of more than 0.41 µm, further 0.42 µm or more, and further 0.45 µm or more, the zirconia sintered body has mechanical strength equal to or higher than the mechanical strength required for a dental material. The average crystal grain size of the sintered body according to an embodiment of the present invention may be 1.5 µm or less and is preferably 1.0 µm or less. The average crystal grain size is preferably 0.55 µm or more and 1.5 µm or less and more preferably 0.6 µm or more and 1.0 µm or less.

The sintered body according to an embodiment of the present invention is preferably a zirconia sintered body having an yttria content of more than 3% by mole and 5.2% by mole or less and an average crystal grain size of 0.42 µm or more. The zirconia sintered body is a so-called translucent zirconia sintered body having higher mechanical strength and higher translucency than the mechanical strength and translucency that are required for a dental material.

The sintered body according to an embodiment of the present invention is obtained by pressureless sintering and has high mechanical strength while having the above large average crystal grain size. Regarding the mechanical strength of the sintered body according to an embodiment of the present invention, the three-point bending strength obtained in accordance with the measuring method described in JIS R 1601 may be 810 MPa or more and is preferably more than 870 MPa, and more preferably 900 MPa or more. In particular, the sintered body according to an embodiment of the present invention has a high three-point bending strength of 900 MPa or more and 1,300 MPa or less, and further 900 MPa or more and 1,200 MPa or less even when the yttria content is 3.8% by mole or more and 4.2% by mole or less, and further 3.8% by mole or more and 4.15% by mole or less.

The sintered body according to an embodiment of the present invention has the above mechanical strength and a total light transmittance of 43% or more, preferably more than 44%, and more preferably 44.5% or more. At an yttria content of more than 3% by mole and 5.2% by mole or less, the total light transmittance may be 49% or less. The total light transmittance in embodiments of the present invention can be measured in accordance with the method described in JIS K 7361 with a D65 light source by using a sintered body having a sample thickness of 1 mm.

Such a zirconia sintered body can be provided as a zirconia sintered body having mechanical strength required for a dental material without impairing translucency of existing zirconia sintered bodies for dental materials and further having higher translucency than translucency of existing zirconia sintered bodies for dental materials. Thus, the zirconia sintered body according to an embodiment of the present invention can be used as a dental material and can be further used as both a dental material for a back tooth and a dental material for a front tooth.

EXAMPLES

The present invention will be specifically described by way of Examples hereinafter. However, the present invention is not limited to these Examples.

Methods for measuring characteristics of sintered bodies and powders according to the present invention will be described below.

(Total Light Transmittance)

The total light transmittance was measured in accordance with the method described in JIS K 7361 by using a turbidimeter (device name: NDH2000, available from Nippon Denshoku Industries Co., Ltd.) with a D65 light source.

A disk-shaped sintered body having a thickness of 1 mm and polished two surfaces was used as a measurement sample.

(Three-Point Bending Strength)

The bending strength was measured by a three-point bending test based on JIS R 1601 "Testing method for flexural strength of fine ceramics". The measurement was conducted 10 times, and the average was defined as a three-point bending strength. The measurement was conducted at a distance between supported points of 30 mm by using a pillar-shaped sintered body sample having a width of 4 mm and a thickness of 3 mm.

(Sintered Body Density)

A measured density of a sintered body was obtained in accordance with the measuring method described in JIS R 1634 (Test methods for density and apparent porosity of fine ceramics). A relative density was obtained from a ratio of the measured density to a theoretical density. Prior to the measurement of the measured density, a pretreatment was performed by measuring the mass of the sintered body after drying, subsequently putting the sintered body into water, and boiling the sintered body for one hour.

The theoretical density ($\rho_0$) was obtained by formula below.

$$\rho_0 = 100/[(A/\rho_A) + (100-A)/\rho_X]$$

In the above formula, $\rho_0$ represents a theoretical density (g/cm³), A represents a content (% by weight) of $Al_2O_3$, $\rho_A$ represents a theoretical density (3.99 g/cm³) of $Al_2O_3$, and $\rho_X$ represents a theoretical density (g/cm³) of an X mol % yttria-containing zirconia sintered body.

$\rho_X$ in the above formula represents different values depending on the crystal phase of the zirconia sintered body. Herein, a value calculated from the formula described in J. Am. Ceram. Soc., 69 [4] 325-32 (1986) (hereinafter, also referred to as a "reference document") can be used as the theoretical density $\rho_X$.

(Average Crystal Grain Size)

The average crystal grain size of a sintered body sample was obtained by the planimetric method from a SEM photograph obtained by a field-emission scanning electron microscope (FESEM). Specifically, a mirror-polished sintered body sample was subjected to thermal etching, and the sample was observed with a field-emission scanning electron microscope (apparatus name: JSM-T220, available from JEOL Ltd.). The average crystal grain size was calculated from the obtained SEM photograph by the planimetric method.

(Yttria Concentration Distribution)

The maximum frequency was measured by using an FE-SEM/EDS (apparatus name: JSM-7600F, available from JEOL Ltd.) as follows. A surface of a sintered body was observed with the SEM at a magnification of 24,000 to obtain a SEM observation image. A ratio of the yttrium concentration relative to the zirconium concentration (Y/Zr ratio) was obtained by measuring EDS spectra at 40,000 positions of the SEM observation image, and quantifying the intensities of characteristic X-rays of zirconium and yttrium. The yttrium concentration distribution was obtained by dividing a range where the Y/Zr ratio exceeded 0.25% into ranges at intervals of 0.5%, and plotting the frequency in each of the yttrium concentration ranges.

Prior to the measurement, the sintered body sample was subjected to Ag sputter coating as a pretreatment.

(Crystal Phase)

XRD measurement of a sintered body sample was conducted by using a common X-ray diffractometer (apparatus name: X'Pert PRO MPD, available from Spectris Co., Ltd.). Conditions for the XRD measurement are described below. The crystal phase of the sintered body sample was identified by subjecting the obtained XRD pattern to Rietveld analysis using RIETAN-2000. The Rietveld analysis of the sintered body sample was conducted under the assumption that the crystal phase included the T phase, the T* phase and the C phase.

| Radiation source: CuKα ray ($\lambda$ = 0.1541862 nm) | |
|---|---|
| Measurement mode | continuous scanning |
| Scan speed | 1°/min |
| Step width | 0.02° |
| Divergence slit | 0.5 deg |
| Scattering slit | 0.5 deg |
| Receiving slit | 0.3 mm |
| Measurement range | 2θ = 10° to 140° |

(Average Particle Size of Powder)

The average particle size of a zirconia powder was measured by using a Microtrac particle size distribution analyzer (apparatus name: 9320-HRA, available from Honeywell Inc.).

A sample powder was suspended in distilled water to prepare a slurry, and the slurry was then subjected to a dispersion treatment with an ultrasonic homogenizer (device name: US-150T, available from NIHONSEIKI KAISHA LTD.) for 3 minutes, as a pretreatment.

Herein, the term average particle size of a zirconia powder refers to a diameter of a sphere having the same volume as a particle having the median diameter, which is a median value of a cumulative curve of a particle size distribution represented on a volume basis, that is, a particle size corresponding to 50% of the cumulative curve. The average particle size is a value measured by a particle size distribution measurement apparatus by a laser diffraction method.

(Crystallite Size of Powder Composition)

The crystallite size of a powder composition was obtained from a main XRD peak by using the formula below.

$$\text{Crystallite size} = \kappa\lambda/\beta\cos\theta$$

In the above formula, κ represents a Scherrer constant (κ=1), λ represents the wavelength of the measured X-ray (λ=1.541862 Å when CuKα rays are used as a radiation source), β represents a full width (°) at half maximum of the main XRD peak, and θ represents the Bragg angle of the main XRD peak.

(Crystal Phase of Powder Composition)

The T+C phase ratio was calculated from an XRD pattern of a crystal phase of a powder composition by using the formula below.

$$T+C \text{ phase ratio } (\%) = 100 - fm(\%)$$

In the above formula, fm represents a monoclinic phase ratio.

(Average Granule Size of Granulated Powder)

The granule particle size of a granulated powder was obtained by a test method for sieve analysis.

Example 1

(Low Yttria Powder)

An aqueous solution of zirconium oxychloride was hydrolyzed to obtain a hydrated zirconia sol. Yttria was added to the hydrated zirconia sol such that the yttria concentration became 2.5% by mole. Subsequently, the resulting mixture was dried and calcined to obtain an yttria-containing zirconia calcined powder. Regarding the calcination conditions, the calcination was conducted in air at 1,160° C. for 2 hours. The resulting calcined powder was washed with distilled water and then dried. Thus, a 2.5 mol % yttria-containing zirconia powder was obtained.

An α-alumina powder having an average particle size of 0.3 μm was mixed with the 2.5 mol % yttria-containing zirconia powder such that the content became 0.05% by weight in terms of $Al_2O_3$ relative to the weight of the zirconia powder. Subsequently, distilled water was added thereto to prepare a slurry, and the slurry was ground and mixed. Thus, a slurry containing a low yttria powder of this Example was obtained. The grinding and mixing were conducted in a water solvent with a ball mill by using zirconia balls having a diameter of 2 mm as grinding media, and the mixing time was 24 hours.

The resulting low yttria powder had an yttria content of 2.5% by mole, an alumina content of 0.05% by weight, a BET specific surface area of 11.2 $m^2/g$ and an average particle size of 0.42 μm.

(High Yttria Powder)

A 5.5 mol % yttria-containing zirconia powder that contained alumina in an amount of 0.05% by weight was obtained by the same method except that yttria was added to a hydrated zirconia sol such that the yttria concentration became 5.5% by mole. This yttria-containing zirconia powder was used as a high yttria powder of this Example.

The resulting high yttria powder had an yttria content of 5.5% by mole, an alumina content of 0.05% by weight, a BET specific surface area of 10.1 $m^2/g$ and an average particle size of 0.40 μm.

(Powder Composition)

The slurry of the low yttria powder and the slurry of the high yttria powder after the grinding and mixing were mixed in a ratio of 50% by weight:50% by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 44 μm and a light-duty bulk density of 1.28 $g/cm^3$. Table 1 shows evaluation results of the powder composition of this Example.

TABLE 1

| | $Y_2O_3$ (mol %) | $Al_2O_3$ (wt %) | BET specific surface area ($m^2/g$) | Average particle size (μm) | T + C phase ratio (%) | Crystallite size (Å) |
|---|---|---|---|---|---|---|
| Example 1 | 4.0 | 0.05 | 10.7 | 0.41 | 68 | 380 |

(Sintered Body)

The resulting powder granules were molded by uniaxial pressing at 19.6 MPa, and then molded by cold isostatic pressing (hereinafter, also referred to as "CIP") at 196 MPa to obtain a green body. The resulting green body was subjected to pressureless sintering in an air atmosphere at a sintering temperature of 1,450° C. and a temperature-increasing rate of 600° C./hr for a holding time of 2 hours. Thus, a zirconia sintered body of this Example having an yttria content of 4.0% by mole was obtained.

The crystal phase of the zirconia sintered body of this Example included only a tetragonal phase. The tetragonal phase included the T phase and the T* phase, and the T*/T ratio was 69.5%.

Table 2 shows evaluation results of the zirconia sintered body of this Example.

Example 2

A zirconia sintered body of this Example having an yttria content of 4.0% by mole was obtained by using the powder composition obtained in Example 1, and the same method as that used in Example 1 except that the sintering temperature was 1,500° C. Table 2 shows evaluation results of the zirconia sintered body of this Example.

Example 3

A zirconia sintered body of this Example having an yttria content of 4.0% by mole was obtained by using the powder composition obtained in Example 1, and the same method as that used in Example 1 except that and the sintering temperature was 1,550° C.

The crystal phase of the zirconia sintered body of this Example included only a tetragonal phase. The tetragonal phase included the T phase and the T* phase, and the T*/T ratio was 81.8%. The maximum frequency of the zirconia sintered body of this Example was 6.9%. FIG. 1 shows the yttrium concentration distribution. [0099]

Table 2 shows evaluation results of the zirconia sintered body of this Example.

Example 4

A green body was obtained by using the powder composition obtained in Example 1 and by the same method as that used in Example 1. The green body was pre-sintered at a pre-sintering temperature of 1,000° C. to obtain a pre-sintered body.

Sintering was conducted by the same method as that used in Example 1 except that the resulting pre-sintered body was used instead of the green body and the sintering temperature was 1,600° C. Thus, a zirconia sintered body of this Example having an yttria content of 4.0% by mole was obtained.

The crystal phase of the zirconia sintered body of this Example included only a tetragonal phase. The tetragonal phase included the T phase and the T* phase. The maximum frequency of the zirconia sintered body of this Example was 6.9%.

Table 2 shows evaluation results of the zirconia sintered body of this Example.

TABLE 2

| | Sintering temperature (° C.) | Theoretical density (g/cm³) | Relative density (%) | Total light transmittance (%) | Three-point bending strength (MPa) | Average crystal grain size (μm) |
|---|---|---|---|---|---|---|
| Example 1 | 1450 | 6.080 | 99.85 | 44.6 | 876 | 0.49 |
| Example 2 | 1500 | 6.080 | 99.87 | 44.5 | 935 | 0.66 |
| Example 3 | 1550 | 6.080 | 99.87 | 44.5 | 1020 | 0.90 |
| Example 4 | 1600 | 6.080 | 99.87 | 44.8 | 1198 | 1.21 |

The above table shows that, in the manufacturing method according to the present invention, with an increase in the sintering temperature, the resulting sintered body exhibits high strength of 900 MPa or more, and further 1,000 MPa or more while having a translucency of 44% or more.

Example 5

(Low Yttria Powder)
A low yttria powder was obtained by the same method as that used in Example 1. The resulting low yttria powder had an yttria content of 2.5% by mole, an alumina content of 0.05% by weight, a BET specific surface area of 11.2 m²/g and an average particle size of 0.41 μm.
(High Yttria Powder)
A high yttria powder was obtained by the same method as that used in Example 1. The resulting high yttria powder had an yttria content of 5.5% by mole, an alumina content of 0.05% by weight, a BET specific surface area of 10.1 m²/g and an average particle size of 0.42 μm.
(Powder Composition)
The slurry of the low yttria powder and the slurry of the high yttria powder after the grinding and mixing were mixed in a ratio of 55% by weight:45 by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 46 μm and a light-duty bulk density of 1.29 g/cm³. Table 3 shows evaluation results of the powder composition of this Example.

TABLE 3

| | $Y_2O_3$ (mol %) | $Al_2O_3$ (wt %) | BET specific surface area (m²/g) | Average particle size (μm) | T + C phase ratio (%) | Crystallite size (Å) |
|---|---|---|---|---|---|---|
| Example 5 | 3.85 | 0.05 | 10.7 | 0.42 | 65 | 380 |

(Sintered Body)
A green body and a sintered body were obtained by the same method as that used in Example 1. Table 4 shows evaluation results of the zirconia sintered body of this Example having an yttria content of 3.85% by mole.

Example 6

A zirconia sintered body of this Example having an yttria content of 3.85% by mole was obtained by using the powder composition obtained in Example 5, and by the same method as that used in Example 4 except that the sintering temperature was 1,500° C. Table 4 shows evaluation results of the zirconia sintered body of this Example.

Example 7

A zirconia sintered body of this Example having an yttria content of 3.85% by mole was obtained by using the powder composition obtained in Example 5, and by the same method as that used in Example 4 except that the sintering temperature was 1,550° C. Table 4 shows evaluation results of the zirconia sintered body of this Example.

TABLE 4

| | Sintering temperature (° C.) | Theoretical density (g/cm³) | Relative density (%) | Total light transmittance (%) | Three-point bending strength (MPa) |
|---|---|---|---|---|---|
| Example 5 | 1450 | 6.083 | 99.84 | 44.9 | 901 |
| Example 6 | 1500 | 6.083 | 99.84 | 44.8 | 961 |
| Example 7 | 1550 | 6.083 | 99.84 | 45.1 | 1078 |

Example 8

(Low Yttria Powder)
A low yttria powder was obtained by the same method as that used in Example 1 except that yttria was added to the hydrated zirconia sol such that the yttria concentration became 3.0% by mole, the calcination temperature was 1,100° C., and the mixing time in the ball mill was 16 hours. The resulting low yttria powder had an yttria content of 3.0% by mole, an alumina content of 0.05% by weight, a BET specific surface area of 13.1 m²/g and an average particle size of 0.40 μm.
(High Yttria Powder)
A high yttria powder was obtained by the same method as that used in Example 1. The resulting high yttria powder had an yttria content of 5.5% by mole, an alumina content of 0.05% by weight, a BET specific surface area of 10.1 m²/g and an average particle size of 0.41 μm.
(Powder Composition)
The slurry of the low yttria powder and the slurry of the high yttria powder after the grinding and mixing were mixed in a ratio of 60% by weight:40 by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 43 μm and a light-duty bulk density of 1.27 g/cm³. Table 5 shows evaluation results of the powder composition of this Example.

TABLE 5

| | $Y_2O_3$ (mol %) | $Al_2O_3$ (wt %) | BET specific surface area (m²/g) | Average particle size (μm) | T + C phase ratio (%) | Crystallite size (Å) |
|---|---|---|---|---|---|---|
| Example 8 | 4.0 | 0.05 | 11.9 | 0.41 | 77 | 370 |

(Sintered Body)

A green body and a sintered body having an yttria content of 4.0% by mole were obtained by the same method as that used in Example 1. Table 6 shows evaluation results of the zirconia sintered body of this Example.

Example 9

A zirconia sintered body of this Example having an yttria content of 4.0% by mole was obtained by using the powder composition obtained in Example 8, and by the same method as that used in Example 7 except that the sintering temperature was 1,500° C. Table 6 shows evaluation results of the zirconia sintered body of this Example.

Example 10

A zirconia sintered body of this Example having an yttria content of 4.0% by mole was obtained by using the powder composition obtained in Example 8, and by the same method as that used in Example 8 except that the sintering temperature was 1,550° C. Table 6 shows evaluation results of the zirconia sintered body of this Example.

TABLE 6

| | Sintering temperature (° C.) | Theoretical density (g/cm³) | Relative density (%) | Total light transmittance (%) | Three-point bending strength (MPa) | Average crystal grain size (μm) |
|---|---|---|---|---|---|---|
| Example 8 | 1450 | 6.080 | 99.87 | 45.0 | 964 | 0.51 |
| Example 9 | 1500 | 6.080 | 99.85 | 45.2 | 1106 | 0.74 |
| Example 10 | 1550 | 6.080 | 99.85 | 45.3 | 1126 | 0.90 |

Example 11

(Low Yttria Powder)

A low yttria powder was obtained by the same method as that used in Example 1. The resulting low yttria powder had an yttria content of 2.5% by mole, an alumina content of 0.05% by weight, a BET specific surface area of 11.2 m²/g and an average particle size of 0.39 μm.

(High Yttria Powder)

A high yttria powder was obtained by the same method as that used in Example 1. The resulting high yttria powder had an yttria content of 5.5% by mole, an alumina content of 0.05% by weight, a BET specific surface area of 10.1 m²/g and an average particle size of 0.40 μm.

(Powder Composition)

The slurry of the low yttria powder and the slurry of the high yttria powder after the grinding and mixing were mixed in a ratio of 45% by weight:55 by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 42 μm and a light-duty bulk density of 1.27 g/cm³. Table 7 shows evaluation results of the powder composition of this Example.

TABLE 7

| | Y₂O₃ (mol %) | Al₂O₃ (wt %) | BET specific surface area (m²/g) | Average particle size (μm) | T + C phase ratio (%) | Crystallite size (Å) |
|---|---|---|---|---|---|---|
| Example 11 | 4.15 | 0.05 | 10.6 | 0.40 | 85 | 380 |

(Sintered Body)

A green body and a sintered body having an yttria content of 4.15% by mole were obtained by the same method as that used in Example 1. Table 8 shows evaluation results of the zirconia sintered body of this Example.

Example 12

A zirconia sintered body of this Example having an yttria content of 4.15% by mole was obtained by using the powder composition obtained in Example 11, and by the same method as that used in Example 11 except that the sintering temperature was 1,500° C. Table 8 shows evaluation results of the zirconia sintered body of this Example.

Example 13

A zirconia sintered body of this Example having an yttria content of 4.15% by mole was obtained by using the powder composition obtained in Example 11, and by the same method as that used in Example 11 except that the sintering temperature was 1,550° C. Table 8 shows evaluation results of the zirconia sintered body of this Example.

TABLE 8

| | Sintering temperature (° C.) | Theoretical density (g/cm³) | Relative density (%) | Total light transmittance (%) | Three-point bending strength (MPa) |
|---|---|---|---|---|---|
| Example 11 | 1450 | 6.078 | 99.88 | 44.7 | 873 |
| Example 12 | 1500 | 6.078 | 99.90 | 45.1 | 929 |
| Example 13 | 1550 | 6.078 | 99.88 | 45.5 | 1049 |

The above table shows that, with an increase in the sintering temperature, even the sintered bodies having an yttria content of more than 4.0% by mole exhibit a strength of 870 MPa or more, further 900 MPa or more, and further 1,000 MPa or more.

Example 14

(Low Yttria Powder)

A low yttria powder was obtained by the same method as that used in Example 8. The resulting low yttria powder had an yttria content of 3.0% by mole, an alumina content of 0.05% by weight, a BET specific surface area of 13.0 m²/g and an average particle size of 0.40 μm.

(High Yttria Powder)

A high yttria powder was obtained by the same method as that used in Example 1. The resulting high yttria powder had an yttria content of 5.5% by mole, an alumina content of 0.05% by weight, a BET specific surface area of 10.0 m²/g and an average particle size of 0.41 μm.

(Powder Composition)

The slurry of the low yttria powder and the slurry of the high yttria powder after the grinding and mixing were mixed in a ratio of 40% by weight:60% by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 45 μm and a light-duty bulk density of 1.29 g/cm³. Table 9 shows evaluation results of the powder composition of this Example.

TABLE 9

|  | Y$_2$O$_3$ (mol %) | Al$_2$O$_3$ (wt %) | BET specific surface area (m²/g) | Average particle size (μm) |
| --- | --- | --- | --- | --- |
| Example 14 | 4.5 | 0.05 | 11.2 | 0.42 |

(Sintered Body)

A green body and a sintered body having an yttria content of 4.5% by mole were obtained by the same method as that used in Example 1. Table 10 shows evaluation results of the zirconia sintered body of this Example.

Example 15

A zirconia sintered body of this Example having an yttria content of 4.5% by mole was obtained by using the powder composition obtained in Example 14, and by the same method as that used in Example 14 except that the sintering temperature was 1,500° C. Table 10 shows evaluation results of the zirconia sintered body of this Example.

Example 16

A zirconia sintered body of this Example having an yttria content of 4.5% by mole was obtained by using the powder composition obtained in Example 14, and by the same method as that used in Example 14 except that the sintering temperature was 1,550° C. Table 10 shows evaluation results of the zirconia sintered body of this Example.

TABLE 10

|  | Sintering temperature (° C.) | Theoretical density (g/cm3) | Relative density (%) | Total light transmittance (%) | Three-point bending strength (MPa) |
| --- | --- | --- | --- | --- | --- |
| Example 14 | 1450 | 6.072 | 99.84 | 46.2 | 815 |
| Example 15 | 1500 | 6.072 | 99.85 | 46.2 | 850 |
| Example 16 | 1550 | 6.072 | 99.82 | 46.4 | 830 |

The above table shows that the sintered bodies having an yttria content of 4.5% by mole each have a strength of more than 800 MPa and exhibit strength suitable for practical application to a dental material, though the strength is lower than those of sintered bodies having an yttria content of 4.0% by mole.

Comparative Example 1

(Low Yttria Powder)

A low yttria powder was obtained by the same method as that used in Example 8. The resulting low yttria powder had an yttria content of 3.0% by mole, an alumina content of 0.05% by weight, a BET specific surface area of 12.9 m²/g and an average particle size of 0.42 μm.

(High Yttria Powder)

A high yttria powder was obtained by the same method as that used in Example 1. The resulting high yttria powder had an yttria content of 5.5% by mole, an alumina content of 0.05% by weight, a BET specific surface area of 9.9 m²/g and an average particle size of 0.43 μm.

(Powder Composition)

The slurry of the low yttria powder and the slurry of the high yttria powder after the grinding and mixing were mixed in a ratio of 10% by weight:90% by weight, and the resulting mixture was sufficiently stirred to obtain a slurry containing a powder composition of this Example. An organic binder was added in an amount of 3% by weight to the slurry containing the powder composition, and the slurry was then spray-dried to obtain a granulated powder. The granulated powder had an average granule size of 43 μm and a light-duty bulk density of 1.28 g/cm³. Table 11 shows evaluation results of the powder composition of this Comparative Example.

TABLE 11

|  | Y$_2$O$_3$ (mol %) | Al$_2$O$_3$ (wt %) | BET specific surface area (m²/g) | Average particle size (μm) |
| --- | --- | --- | --- | --- |
| Comparative Example 1 | 5.25 | 0.05 | 10.2 | 0.43 |

(Sintered Body)

A green body and a sintered body having an yttria content of 5.25% by mole were obtained by the same method as that used in Example 1. The sintered body of this Comparative Example has a three-point bending strength of 613 MPa and does not have a bending strength necessary for a dental application, showing that a zirconia sintered body having an yttria content of more than 5.2% by mole has low mechanical strength.

Comparative Example 2

An aqueous solution of zirconium oxychloride was hydrolyzed to obtain a hydrated zirconia sol. A zirconia powder was obtained by the same method as that used for the low yttria powder of Example 1 except that yttria was added to the hydrated zirconia sol such that the yttria concentration became 4.0% by mole. This zirconia powder was used as a zirconia powder of this Comparative Example.

The resulting low yttria powder had an yttria content of 4.0% by mole, an alumina content of 0.05% by weight, a BET specific surface area of 11.2 m²/g and an average particle size of 0.41 μm.

A green body and a sintered body having an yttria content of 4.0% by mole were obtained by the same method as that used in Comparative Example 1 except that the zirconia powder of this Example was used and the sintering temperature was 1,550° C.

Figure 2:
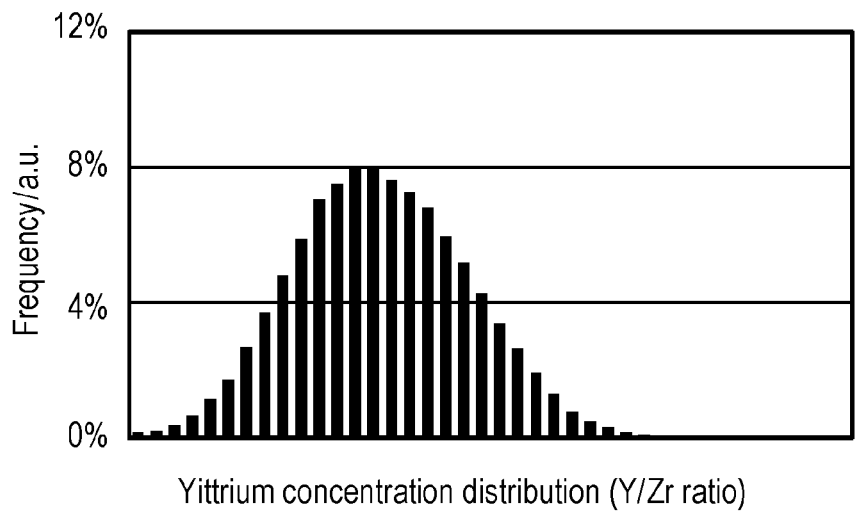
FIG. 2 A graph showing the yttrium concentration distribution of Comparative Example 2.

The crystal phase of the zirconia sintered body of this Comparative Example included only a tetragonal phase. The tetragonal phase included the T phase and the T* phase, and the T*/T ratio was 75.4%. The maximum frequency of the zirconia sintered body of this Comparative Example was 8.0%. FIG. 2 shows the yttrium concentration distribution.

The sintered body of this Comparative Example had a total light transmittance of 45.3% and a three-point bending strength of 870 MPa. This is lower than the strength of the sintered body of Example 11, which had an yttria content of 4.1% by mole and was obtained at the same sintering temperature. Furthermore, the bending strength of this Comparative Example had a minimum of 703 MPa and thus varied widely. These results show that the manufacturing method according to the present invention can provide a sintered body having a higher strength than existing sintered bodies. In addition, the sintered body of this Comparative Example had a high T*/T ratio, showing that yttria was distributed more uniformly than that in the sintered bodies of Examples.

INDUSTRIAL APPLICABILITY

The method for manufacturing a zirconia sintered body according to the present invention can be provided as a method for manufacturing a zirconia sintered body having both high translucency and high mechanical strength with high repeatability. Furthermore, the zirconia sintered body can be used as both a dental material for a front tooth and a dental material for a back tooth.

What is claimed is:

1. A method for manufacturing a zirconia sintered body, the method comprising molding a powder composition that has a yttria content of more than 3% by mole and 5.2% by mole or less and that contains a first zirconia powder having a yttria content of 2% by mole or more and 3.5% by mole or less and a second zirconia powder having a yttria content of more than 4% by mole and 6% by mole or less to obtain a green body; and sintering the green body to obtain a sintered body, and
wherein a content ratio of the second zirconia powder to the first zirconia powder is second zirconia powder: first zirconia powder=20% by weight: 80% by weight to 80% by weight: 20% by weight.

2. The manufacturing method according to claim 1, wherein the powder composition contains alumina.

3. The manufacturing method according to claim 1, wherein the powder composition has a BET specific surface area of 5 m²/g or more and less than 17 m²/g.

4. The manufacturing method according to claim 1, wherein a weight ratio of the first zirconia powder to the second zirconia powder is 35% by weight: 65% by weight to 65% by weight: 35% by weight.

5. The manufacturing method according to claim 1, wherein the first zirconia powder has an yttria content of 2% by mole or more and 3.5% by mole or less, and the second zirconia powder has an yttria content of 4.5% by mole or more and 5.7% by mole or less.

6. The manufacturing method according to claim 4, wherein a sintering temperature in the sintering step is 1,400° C. or higher and 1,600° C. or lower.

7. A powder composition comprising a yttria content of more than 3% by mole and 5.2% by mole or less and that contains a first zirconia powder having a yttria content of 2% by mole or more and 3.5% by mole or less and a second zirconia powder having an yttria content of more than 4% by mole and 6% by mole or less, and
wherein a content ratio of the second zirconia powder to the first zirconia powder is second zirconia powder: first zirconia powder=20% by weight: 80% by weight to 80% by weight: 20% by weight.

8. The powder composition according to claim 7, wherein an alumina content is 0% by weight or more and 0.1% by weight or less.

9. The powder composition according to claim 7, wherein a crystallite size of the powder composition is 200 Å or more and 400 Å or less.

10. The powder composition according to claim 7, wherein a BET specific surface area is 5 m²/g or more and less than 17 m²/g.

11. A method for producing a green body comprising forming a powder composition that has an yttria content of more than 3% by mole and 5.2% by mole or less and that contains a first zirconia powder having an yttria content of 2% by mole or more and 3.5% by mole or less and a second zirconia powder having an yttria content of more than 4% by mole and 6% by mole or less, to obtain a green body, and
wherein a content ratio of the second zirconia powder to the first zirconia powder is second zirconia powder: first zirconia powder=20% by weight: 80% by weight to 80% by weight: 20% by weight.

12. A method for producing a pre-sintered body comprising heat-treating a powder composition that has an yttria content of more than 3% by mole and 5.2% by mole or less and that contains a first zirconia powder having an yttria content of 2% by mole or more and 3.5% by mole or less and a second zirconia powder having an yttria content of more than 4% by mole and 6% by mole or less, to obtain a pre-sintered body, and
wherein a content ratio of the second zirconia powder to the first zirconia powder is second zirconia powder: first zirconia powder=20% by weight: 80% by weight to 80% by weight: 20% by weight.

* * * * *